United States Patent
Martin

(10) Patent No.: US 9,006,216 B2
(45) Date of Patent: *Apr. 14, 2015

(54) BIOCIDAL ALDEHYDE COMPOSITION FOR OIL AND GAS EXTRACTION

(76) Inventor: Howard Martin, Potomac, MD (US)

( * ) Notice: Subject to any disclaimer, the term of this patent is extended or adjusted under 35 U.S.C. 154(b) by 420 days.

This patent is subject to a terminal disclaimer.

(21) Appl. No.: 13/311,815

(22) Filed: Dec. 6, 2011

(65) Prior Publication Data

US 2012/0087993 A1   Apr. 12, 2012

Related U.S. Application Data

(63) Continuation-in-part of application No. 12/584,650, filed on Sep. 9, 2009.

(60) Provisional application No. 61/562,812, filed on Nov. 22, 2011.

(51) Int. Cl.
| | |
|---|---|
| *A01N 57/00* | (2006.01) |
| *A01N 57/20* | (2006.01) |
| *A01N 35/04* | (2006.01) |

(52) U.S. Cl.
CPC ............... *A01N 57/20* (2013.01); *A01N 35/04* (2013.01)

(58) Field of Classification Search
None
See application file for complete search history.

(56) References Cited

U.S. PATENT DOCUMENTS

| | | | | |
|---|---|---|---|---|
| 4,353,806 | A * | 10/1982 | Canter et al. | 507/229 |
| 5,128,051 | A * | 7/1992 | Theis et al. | 210/764 |
| 5,252,606 | A * | 10/1993 | Martin | 514/574 |
| 7,231,976 | B2 * | 6/2007 | Berry et al. | 166/291 |
| 2011/0060052 | A1 | 3/2011 | Martin | |

FOREIGN PATENT DOCUMENTS

| | | | |
|---|---|---|---|
| CA | 1262667 | A1 * | 11/1989 |
| CN | 1664048 | A * | 9/2005 |
| JP | 2000290112 | A * | 10/2000 |

OTHER PUBLICATIONS

"Pluronic PE types" Technical Information, Mar. 2005, published by the BASF Chemical Company.*
Shackelford et al., Use of a New Alginate Film Test to Study the Bactericidal Efficacy of the High-Level Disinfectant Ortho-Phthalaldehyde, Journal of Antimicrobial Chemotherapy, 57(2):335-338 (2006).

* cited by examiner

*Primary Examiner* — Abigail Fisher
*Assistant Examiner* — Daniel L Branson
(74) *Attorney, Agent, or Firm* — Ober, Kaler, Grimes & Shriver; Royal W. Craig

(57) ABSTRACT

A combination biocide (Glutaraldehyde or OPA), quaternary phosphonium biocide (preferably TTPC), alcohol (preferably isopropyl alcohol), and functional excipients for the oil and gas recovery industry. The functional excipients for the oil and gas recovery industry are a cellulose type proppant, a poloxamer wetting agent, a friction-reducing pluronic block copolymer, a drag reducing agent such as polyethylene oxide, and a flocculating agent. The OPA may be of the dialdehyde $C_6H_4(CHO)_2$ form, and the Glutaraldehyde of formula $C_5H_8O_2$. Both will produce an inherent bacteriostatic effect and lower surface tension and thus aids in the spread of the TTPC on the biofilm covered surface where it is readily absorbed by the negative surfaces of proteins and bacteria. It thus serves as a binding agent between the TTPC and the application surface. The foregoing constituents are combined in preferred concentrations within acceptable ranges to provide a synergistic biological chemical complementarity system.

7 Claims, No Drawings

BIOCIDAL ALDEHYDE COMPOSITION FOR OIL AND GAS EXTRACTION

CROSS-REFERENCE TO RELATED APPLICATION(S)

The present application derives priority from U.S. provisional application Ser. No. 61/562,812 filed 22 Nov. 2011, and is a continuation-in-part of U.S. patent application Ser. No. 12/584,650 filed Sep. 9, 2009.

BACKGROUND OF THE INVENTION

1. Field of the Invention

The present invention relates to chemical disinfection and sanitizing and, more particularly, to an improved biocidal aldehyde composition particularly suited for secondary oil and gas recovery.

2. Description of the Background

The purpose of disinfection is to reduce microbial contamination to an innocuous level. There is a widespread need for effective antimicrobials across diverse industries, including for oil and gas recovery (for treatment, penetration and removal of biofilm). Without a biocide, microorganism growth leads to biofilm formation, which contributes to corrosion, contamination of oil and gas, and degradation of drilling muds and fracturing. There are a few existing commercial biocides that purport to solve the need. For example, Dow® sells a line of AQUCAR™ water treatment microbiocides which include various proportions of glutaraldehyde alone or in combination with other biocides such as acetone or ammonium chloride. Glutaraldehyde is an important high level disinfectant/sterilant also used in other industries such as health care. It requires time and temperature control (residence time of 45-90 minutes for disinfection, and controlled temperature of from 20 C to 25-30 C). Glutaraldehyde requires activation and dating to make it useful. Thus, proper usage entails a three step procedure and meticulous record-keeping regarding date of activation.

A different aldehyde, ortho-phthalaldehyde (OPA), has now come into use in the health care industry. Johnson and Johnson developed an original formulation in the late 1980s described in U.S. Pat. No. 4,851,449 and in subsequent continuation in part application(s). This OPA has been approved by the FDA as a high level disinfectant with a twelve minute disinfection time at 20-22 degrees C. Its sterilization time is listed between 24-32 hours. OPA interacts with amino acids and proteins of microorganisms. OPA is lipophilic, which improves its uptake in the cell walls. Thus, OPA has been shown to be another effective disinfectant/sterilant. The J&J OPA concentration is 0.55% by weight at a pH 3-9. It has been shown to be effective in a purely aqueous immersion solution. Metrex Research Corp. continues to sell a modified formulation referred to as OPA+, with an increased OPA concentration of 0.6% (0.05% more OPA), plus buffers, a corrosion inhibitor, and a chelating agent. In essence the formula is the same as the J&J product, with no faster kill time, but claims of 60% more treatment. However, if one looks at the mechanism by which OPA works it becomes biologically clear where the weaknesses lie. OPA is an aromatic dialdehyde. The severe test for cidal effectiveness are gram negative bacteria, mycobacteria and spore-coated organisms. OPA is not completely effective in clinical use at its concentration of 0.5% and pH 6.5. Failures occur and have been reported in literature surveys. The benzene ring of OPA is a planar, rigid structure. Therefore, OPA has no flexibility as a result of steric hindrance. In addition, OPA only reacts with primary amines.

OPA is bactericidal at low concentrations to staphylococci and gram negative bacteria. The poor sporicidal activity is due to low concentration and low pH. It has been noted that if the temperature is raised from the normal 20 degrees C. to 30 degrees it improves. However, this is impractical. Regarding mycobacteria, a similar problem is present. The lipophilic aromatic component of OPA does not reliably penetrate the lipid-rich cell wall of mycobacteria and gram negative bacteria. Indeed, subsequent studies show that OPA exhibits selective bactericidal activity, good against *Pseudomonas aeruginosa*, limited activity against mycobacterial strains. See, Shackelford et al., *Use of a New Alginate Film Test To Study The Bactericidal Efficacy Of The High-Level Disinfectant Ortho-Phthalaldehyde*, Journal of Antimicrobial Chemotherapy, 57(2):335-338 (2006). Despite the lingering issues, OPA has been suggested for use as a biocide in oil and gas recovery applications. See, U.S. Pat. No. 5,128,051 to Theis et al. issued Jul. 7, 1992 which discloses providing ortho-phthalaldehyde to aqueous systems susceptible to biofouling, including secondary oil recovery processes.

Presently, there is no single universally effective biocide due to variable physical, chemical and biological parameters. A biocide must have interactions of a variegated nature in order to have a chance of reasonable effectiveness. What is needed is a simple and improved one-step formulation.

In copending U.S. patent application Ser. No. 12/584,650 filed Sep. 9, 2009 the present inventor suggests a synergistic combination of quaternary ammonium cations with an aldehyde selected from the group consisting of glutaraldehyde and orthophthalaldehyde, isopropyl alcohol, chlorine dioxide ($ClO_2$), a proppant comprising a cellulosic compound selected from the group consisting of methylcellulose, ethylcellulose and hydroxymethylcellulose, a pluronic block copolymer, a flocculating agent, and water. The present inventor has established that the goal can be accomplished more effectively with combinations of tributyl tetradecyl phosphonium chloride (TTPC) (or, alternatively, tetrakis (hydroxymethyl) phosphonium sulfate (THPS)), with the following biocides: glutarladehyde, orthophthalaldehyde and/or isopropyl alcohol.

Thus, the present application discloses an improvement to the preceding formulation in which a quaternary phosphonium salt, preferably tributyl tetradecyl phosphonium chloride (TTPC), is substituted for the dual chain quaternary ammonium to achieve markedly improved results. Alternatively, Tetrakis (hydroxymethyl) phosphonium sulfate (THPS) may be used in lieu of TTPC. The following discussion is explanatory and evidenced based using either glutaraldehyde or OPA for more effective disinfection/sterilization in industrial/commercial uses such as oil and gas recovery.

TTPC has improved thermal and chemical stability based upon its unique miscibility and solvating properties. TTPC is less dense than water and is anion dependent, which makes it sensitive to various solutes and thereby a better component carrier for the glutaraldehyde, OPA, IPA, $ClO_2$. It also enhances catalysis. TTPC is a phosphonium salt with the phosphonium ion ($PH4+$) replacing the amine of the dual chain quat formulation. The quat to be replaced had a tendency to foam especially above pH8. The mechanism of kill is cationic whereby an electrostatic bond is formed with the cell wall affecting permeability and denaturing proteins. The effective pH is 6-8.5 and is only bacteriostatic.

TTPC is a broad spectrum biocide of the alkyl phosphonium group. TTPC is cationic also but with low foaming tendency, a high level of hydrolytic stability, and it functions over a much broader pH range from 2-11. TTPC damages cell walls, as explained further, and affects cell enzyme process.

TTPC is not affected by brine as is the dual chain quat formulation making it superior for oil field usage. TTPC kills at much lower concentrations than the dual chain quat formulation and is faster acting. TTPC aids in biofilm penetration and delays biofilm regrowth, which is extremely meaningful for oil/gas usage. TTPC is a neoteric solvent/biocide that has been developed with remarkable individual properties. It is an ionic liquid that has microbicidal qualities, solvent qualities, and detergent qualities.

SUMMARY OF THE INVENTION

It is, therefore, an object of the present innovation to provide a novel strategy for potentiating and improving the cidal effectiveness of orthophthalaldehyde or glutaraldehyde by a synergistic formulation that combines cidal molecules with a biological chemical system that actively transports itself into the cells, through the biofilm and cell wall/membranes, thereby overcoming penetration restraints.

It is another object to improve cidal effectiveness against a broader range of refractory microorganisms within ecological and environmentally acceptable parameters, essentially yielding a green biocide.

In one embodiment designed for the oil and gas industry, these and other objects are accomplished by a novel combination of glutaraldehyde or OPA, a quaternary phosphonium biocide, alcohol, a proppant, friction reducing chemical additive, wetting agent, drag reducing agent, and flocculating agent. The quaternary phosphonium biocide is preferably tributyl tetradecyl phosphonium chloride (TTPC), though tetrakis (hydroxymethyl) phosphonium sulfate (THPS) may also be used. The alcohol is preferably isopropyl alcohol. The OPA is the dialdehyde $C_6H_4(CHO)_2$, which produces an inherent bacteriostatic effect and lowers surface tension and thus aids in the spread of the TTPC on the biofilm covered surface where it is readily absorbed by the negative surfaces of proteins and bacteria. It thus serves as a binding agent between the TTPC and the application surface. Rather than OPA, a glutaraldehyde may be substituted in conjunction with the other constituents. The foregoing constituents are combined in preferred concentrations within acceptable ranges to provide a synergistic formulation that combines cidal molecules with a biological chemical system that actively transports itself into the cells, through the biofilm and cell wall/membranes, thereby overcoming penetration resistance.

TTPC, in conjunction with the aforementioned single biocides, creates a unique and surprisingly more effective biocidal combination than the cationic amine based dual, chain quats. These new formulations now create an outstanding synergistic interaction due to the new reactive chemistry of the ionic solvent, and improves kill and kill time, without the need for activation or any time or temperature control.

Other objects, features, and advantages of the present invention will become more apparent from the following detailed description of the preferred embodiments and certain modifications thereof.

DETAILED DESCRIPTION OF THE PREFERRED EMBODIMENT

The present invention is a solution with a synergistic complementarity of constituents that combine to improve the cidal effectiveness of glutaraldehyde or orthophthalaldehyde through a biological chemical system to provide improved results. The present invention allows a one-step formulation for disinfection/sterilization for industrial/commercial uses and especially secondary oil and gas recovery, by addition to fracturing (frac) water as an aqueous solution additive. The unique chemo-biological formulation described herein improves the cidal effectiveness of Glutaraldehyde or OPA by the addition of a quaternary phosphonium biocide, TTPC, along with a proppant, friction reducing chemical additive, wetting agent, drag reducing agent, and flocculating agent, the foregoing combination creating a synergistic and unexpected improvement in biocidal effectiveness resulting in faster kill time.

The oil and gas recovery industry has a need for treatment, penetration and removal of biofilm. Biofilm harbors bacteria that attack surfaces such as steel, and that coalesces with oil in pipelines causing blockage. Biofilm occurs naturally by the bacteria, fungii, algae, protozoa developing it, as a protective mechanism. Surface microorganisms exist in planktonic suspension rather than in biofilm and are easier to kill. The biofilm exist in an exopolysaccharide matrix thereby having different characteristics than the planktonic types. This requires a biochemical approach rather than a purely chemical biocide as in the prior art.

In copending U.S. patent application Ser. No. 12/584,650 the dual chain quaternary ammonium aids in the destruction and prevents proliferation of desulfovibrio desulfuricans (SRBs) of injected water in oil and gas recovery. When injected the quats spread through the subterranean sand structures containing residual oil and displace the oil in the direction of the producing well. However, the dual chain quat is a molecular solvent rather than a completely ionic solvent, as is tributyl tetradecyl phosphonium chloride (TTPC). Therefore the outcome reactions are different. The substitution of TTPC for the dual chain quat results in different thermodynamics and kinetics, and improved synergism and killing. The biocidal results are 2× to 4× more effective, and toxicity is reduced.

The Glutaraldehyde or OPA in combination with the TTPC work in synergy to kill the SRBs more effectively. Several groups have reported that biofilm bacteria exhibit more resistance to biocides. As in medicine, industrial surfaces (such as surfaces of storage tanks, pipelines, water circulating systems, and machinery) become colonized by biofilms. It is known that the anionic polysaccharide matrix (glycocalyx) affords considerable protection to these cells against antimicrobial agents. Essentially a physical barrier is erected against the penetration of the biocide. Along with the barrier concept other biological mechanisms are also involved such as enzyme formation, reduction of metabolism through quiescence, and general stress response leading to a new general biofilm phenotype. Thus, the oil and gas industry has a severe biofouling problem with the development of biofilm along with sulfate reducing bacteria that creates significant damage. The basic strategy of biofilm control is predicated on the use of chemicals to kill bacteria in the biofilm, to induce the natural sloughing of dead biofilm thus cleaning the surface. The chemical approach suffers from the limitation that the most effective antimicrobial agents do not penetrate the biofilm. It is very difficult to deliver enough cidal agent to destroy the bacteria within the biofilm, the sessile organisms. These insidious and coated bacteria must be destroyed in order for water pipelines to function and clean the oil. The biofilm contains amongst its variety of microorganisms, SRBs, algae, fungi, aerobic, anaerobic and facultative bacteria. Planktonic type bacteria exist in an aqueous phase and are relatively easy to kill. It is however, the extracellular polymeric material that protects the attached or contained sessile organism that is the difficult one to eradicate. It is with these protected organisms that the present formulation excels, attacking and achieving the desired kill effect. It is noteworthy that in the industrial context the efficacy improves as the temperature rises. The illustrative tests were run at 20-22 C but the one test run at 25-30 C showed a significant reduction in time.

Currently, in the oil and gas recovery business, companies employ calibrated force to control the biofilm by overcoming the tensile strength of the matrix material without damaging the integrity of the surface. Hydraulic fracture or "fracking" is used to initiate oil and gas production in the shale recovery area. Fracking uses the hydrodynamic shear of water pump pressure to create fractures that extend from a borehole into rock formations. The fractures are maintained open by a proppant (a propping agent), usually a granular substance such as sand or mechanical such as aluminum pellets or ceramic, which prevent the fractures from closing. This is typically used in low permeability reservoirs and/or to re-stimulate production in old wells. To enhance recovery, the fracking technique is used with what is a slick water frac. This begs the need for a friction reducing chemical additive to allow water to be pumped faster and deeper into the formation. A secondary requirement is the need for a proppant that is biodegradable and will not clog or block the fluid. Therefore, a combination biocide, biodegradable proppant, and a soluble friction reducer would serve well. The above-described formulation may be modified slightly to provide an unconventional formula approach to this problem.

In accordance with the present invention, a core biocide either OPA of the dialdehyde $C_6H_4(CHO)_2$ form, or Glutaraldehyde of formula $C_5H_8O_2$, in alcohol-solution form, is modified by combining TTPC, Isopropyl Alcohol, and other functional excipients specifically for the oil and gas recovery industry. Specifically, the modification entails the addition of a proppant, friction reducing chemical additive, wetting agent, drag reducing agent, and flocculating agent to the above-described formulation, preferably replacing a small portion of the alcohol.

The proppant of choice is a cellulose type, preferably a water soluble binder such as methylcellulose, ethylcellulose or hydroxymethylcellulose, which serve as an inactive filler, thickener and stabilizer. These materials are hydrophilic and highly absorbent thereby making an excellent proppant of a purely biologic non-toxic nature. Its biodegradability and natural occurrence makes this addition to the environment and ecosystem a green component. Being a straight chain polymer it becomes an extended stiff rod like formation. It forms via this conformation a micro fibril with high tensile strength because the hydroxyl group on the glucose molecule combines with oxygen molecules through a hydrogen bond thus giving shape, form and strength. Methylcellulose has value in zones of high heat as heat solidifies it giving it form and substance. It has inherent lubricity. Its derivatives can aid in water retention, surface slip resistance and maintain open time. A particular form, microcrystalline cellulose compacts well under high pressures and has a high binding capacity. It is hard, stable and yet can disintegrate rapidly. Cellulose is an ideal proppant excipient.

Furthermore, in order to facilitate the deep penetration by reduced frictional drag the addition of a wetting agent is required, and a poloxamer is preferred. This creates a high velocity hydro miscible vehicle. Poloxamers are nonionic triblock copolymers composed of a central hydrophobic chain of polyoxypropylene (poly(propylene oxide)) flanked by two hydrophilic chains of polyoxyethylene (poly(ethylene oxide)).

A monomeric polymer, preferably a pluronic block copolymer, is also added as a friction reducer for oil and gas recovery. The importance of this excipient and cellulose is recognized. Aqueous solutions of block copolymers are stable, soluble and exist as monomolecular micelles. They decrease surface tension as well as surface free energy. They reduce proppant flowback by strengthening the cellulose molecular structure. In oil and gas recovery the pluronic prevents the flowback via the proppant by its inherent adhesiveness. This also helps in agglomeration of the proppant.

The hydrodynamic flow may also be increased by improving flowability and penetration, thereby enhancing the shear forces. To achieve this, a drag reducing agent such as polyethylene oxide may be used. What is required of the drag reducer is an agent that has a low coefficient of friction, low film thickness, and should be thixotropic or rheopectic. It needs to be effective at either low or high velocity for frac fluid usage. A fixed film thickness is necessary due to constant loading as well as low compressibility. What works is a water soluble resin such as a nonionic, high molecular weight water-soluble poly(ethylene oxide) polymer that brings lubricity, water retention, film formation and thickening into play. Dow® Polyox™ is an ideal brand of polyethylene oxide. This enables frac fluid to transport itself and penetrate deep into fractures. Polyox™ as a slip and drag reducer is compatible with the TTPCs used by the above-described formula. They show little degradation at high pressure turbulence making them an ideal additive to the formulation. A reduction of splattering viscoelasticity is also necessary, and Polyox™ is an ideal flocculating agent for this purpose. It enables frac fluid to transport itself and penetrate deep into fractures.

In accordance with the present invention, a core glutaraldehyde or OPA is combined with the above-described TTPC, Isopropyl Alcohol, and other functional excipients for the oil and gas recovery industry. Preferably, the core Glutaraldehyde or OPA, TTPC, Isopropyl Alcohol and functional excipients are combined in the following preferred concentrations within acceptable ranges:

| Constituent | % by weight | Acceptable Range |
| --- | --- | --- |
| OPA or Glutaraldehyde | 5% | 0.25-7% |
| TTPC[1] | .48% | .24-6% (50-1000 ppm) |
| Isopropyl Alcohol | 41% | 10-60% |
| methylcellulose, ethylcellulose or hydroxymethylcellulose | 0.4% | 0.2-0.5% by weight |
| pluronic block copolymer | 0.7% | 0.01% to 3.00% by weight |
| poly(ethylene oxide) (Polyox ™) | 50 ppm or 0.5% | 10 ppm to 100 ppm (.1-1%) |

[1] An equal amount of tetrakis (hydroxymethyl) phosphonium sulfate (THPS) should be used if substituted for TTPC.

The balance of the solution is primarily water, plus inert additives as desired including Triethanol Amine, Glycol Ether, and Sulfonic Acid. The pH range throughout can be pH 3 to pH 9.

The following examples illustrate the efficacy of the above-described embodiment in a formulation without the addition of a proppant, friction reducing chemical additive, wetting agent, drag reducing agent, or flocculating agent:

EXAMPLES

When TTPC was added to the core Glutaraldehyde or OPA as a substitute for dual chain quaternary ammonium the effective kill time was twice as fast (2×) based upon log reduction. Similarly, the TTPC reduced the effective kill time of acid-producing bacteria (APB) by almost 50%. Although the kill speed of TTPC alone was 20% slower than the glut/quat formula of copending U.S. patent application Ser. No. 12/584,650, when TTPC is combined with glutaraldehyde as a substitute for dual chain quaternary ammonium the kill time increased to four times 4× faster, evidencing the synergism of the present combination.

Another test with the organism of Pseudomonas aeruginosa was carried out using a suspension of $10^4$ ml of the present formulation with 5% serum added as bioburden. The suspension was exposed to TTPC/glutaraldehyde and TTPC/OPA embodiments in concentration of from 50 ppm 100 ppm, 500 ppm, 1,000 ppm for periods of 4 hours, 1 hour, and 30 minutes. The results showed complete kill in all time frames and at all concentrations. This test was repeated at concentrations of $10^5$ ml and $10^6$ ml. The results were similar illustrating that the concentration of bacteria did not require titration of biocide. The effective range of bactericidal activity for incorporation of TTPC within the varied glutaraldehyde or OPA materials was from 50 ppm to 1000 ppm.

A test with chlorine dioxide ($ClO_2$) and TTPC versus Pseudomonas aeruginosa was performed at $10^5$ ml with $ClO_2$ of 10 ppm. This alone gave a 1 log reduction in 30 min exposure. TTPC alone at 50 ppm gave a 2 log reduction. The combination of $ClO_2$ and TTPC of 5 ppm and 10 ppm gave a 5 log reduction in 30 min. The synergy of $ClO_2$ and TTPC is much more effective than the individual components.

Isopropyl alcohol (IPA) and quaternary ammonium kill Pseudomonas in $10^6$ mil in 2 min with concentrations of 0.24% and IPA 41.5%. A mixture of 18% IPA and 0.10% TTPC was compared in rate of kill at 2 minutes with $10^6$ ml of Pseudomonas. The kill was 0 failures in 60 tubes. This again shows the unusual strength of synergy of TTPC with the various tested biocides. The IPA was important as this formulation has a high volatile organic compound (VOC) issue. By reducing the alcohol and TTPC level it will fall within more healthy parameters.

As a result of the foregoing cidal effects, the synergy index was between 0.6 and 0.8 (below 1.0 indicates synergy effectiveness) for the various combinations of chemistries. This illustrates a notably-significant improvement in bactericidal effectiveness.

Comparing the glutaraldehyde/quaternary ammonium formulation to glutaraldehyde/TTPC of the present formulation the rate of kill was faster by 1 log in 30 min but the concentration of TTPC was 50% less than the quat amine in the prior formulation. Thus, there is improved cidal and ecological result in the oilfield context. The OPA/quat versus OPA/TTPC of the present formulation reacted in similar fashion during testing. Both Glut and OPA embodiments of the present invention can be reduced overall by 10%, and the TTPC (versus quaternary ammonium component) can be reduced by 50%. Clearly this is a safer more ecological biocide for both oil/gas and medical usage.

TTPC is less volatile thereby reducing the release of VOCs. Thus, the present formulation is a tailored solvent micro biocide that optimizes cidal effectiveness as well as decreases ecological toxicity. The formulation also exhibits more stable thermal conditions, remaining liquid in a range of 300 C (−96 to 200 C), working in a pH range of 2-12, succeeds in solvating organic, inorganic and polymeric materials, catalyzes, and is very miscible in the present solution.

In the particular context of biofilm reduction in secondary oil and gas recovery, TTPC has superior biofilm removability compared to quaternary ammonium. As such there is actually a slight increase in planktonic microbes which are more susceptible to biocide/TTPC effects. Individual biocides affect the physiology of the cell quite differently. Understanding and elaborating their effects allows for a more intelligent (safe and effective) and innovative combination of mechanistically different agents so that a more effective and efficient formulated compound is developed. The present combination of chemicals creates an improved general synergy of action resulting in a more efficient and targeted application of a biocide mixture rather than multiple single biocides, surprisingly and significantly adding to the synergistic effectiveness of the biocidal combinations with TTPC of Glutaraldehyde, Ortho-phthalaldehyde, Isopropyl Alcohol, Chlorine Dioxide, separately in individual formulation. This is an example of enhanced quantum complementarity. The importance of the environmental parameter cannot be underestimated based upon the foregoing results. TTPC has a similar margin of exposure as the quats for oil field imputability with friction reducers for killing of aerobic organisms. However, TTPC is twice as effective as the original glut/quat formula and improves the OPA/quat blend based upon a 5 log reduction in oil frac water. OPA/Quat blend vs. the replacement of Quat with TTPC, diluted to 1,000 ppm is essentially non-corrosive to metals including stainless steel. The minimum inhibitory concentration (MIC) for the TTPC usage is 50-500 ppm. Therefore it is safe regarding corrosiveness, an important facet in well treatment. Efficacy in oil/gas fields shows glut/quat and TTPC alone to be almost equally effective on sulfur reducing bacteria (SRB). The faster cidal action is due basically to the chemistry difference between amine quats and phosphonium salts. The ammonium quats have longer alkyl chains. Instead of amine the difference is a phosphonium ion but also importantly is the alkyl chain length. It has been determined that there is an optimal length for anti-bacterial effectiveness. It was dependent upon chain length and attachment moieties. It was unexpected that the tetradecyl group exhibited the broadest spectrum of activity against the tested microorganisms MRSA, B. subtillis (which are gram +), E. coli, pseudomonas aeruginosa (gram −); candida a fungus, based upon specific chain length. Usually the longer chain was better but not in these cases. The ammonium quat did not kill all the test bacteria in the allotted time of 30 minutes. TTPC did. There are great differences between Gram + and Gram − bacteria in their cell walls. Gram + possess a mesh-like wall of peptidoglycan and teichoic acid. The Gram − wall is complicated. It has in addition to the wall of G+ an outer membrane of lipopolysaccharides and phospholipids that protect the cell.

What is referred to as the S layer adheres to the cell outer membrane. Its pattern is tile-like and associated with the peptidoglycan layer. This layer is susceptible to ion formation and osmotic stress. By attacking this layer the self-assembly ability of cell protection is reduced. This disrupts the glycocalyx (both the capsule and slime/biofilm layer) of the cell.

Capsules outside the cell wall are polysaccharides. As such they contain a great deal of water and protect against hydrophobic biocides. This is why TTPC being amphiphilic is effective—it being both hydrophobic and hydrophilic. Interestingly, the phospholipids themselves are amphiphilic. The membrane proteins are of two types—peripheral (easily disrupted) and integral (not so). Integral proteins are essential for cell function. TTPC is unusually suited for affecting these proteins by being amphipathic.

The length of the biocide alkyl chain creates a hydrophobic tail. By adjusting the chain as in TTPC, it becomes able to interact with the cytoplasm membrane which is the target site of cationic biocides. However the TTPC worked with a somewhat shorter chain contrary to expectation. Generally the concentration and structure of the surfactant affects the aggregates organization so that amphiphiles (TTPC) give very different morphologies. The chain length of antibacterial activity is based upon micelle aggregation in solution. The optimal alkyl chain length affects the critical micelle concentration (CMC). The ability to rupture the membrane cell wall thereby giving access to the cytoplasmic membrane is key. The rearrangement of the molecular cell wall to form a channel space with enough radius to allow access of the Gluteraldehyde, OPA, IPA, $ClO_2$ all with TTPC requires sufficient rupturing for molecular insertion within the cell itself. This disruption is based upon lowering surface tension and bending rigidity weakening based upon negative bubble curvature. This ability to create interfacial fluctuations in the membrane is the hole-nucleation theory of Kabalnov and Wennerstrom (Langmuir, 1996). Access is granted to the inner cytoplasmic membrane made of phospholipids and proteins (phosphoglycerides) similar to Gram + as well as Gram − cells. This access is due to the presence of porin proteins. They form trimers in the outer membrane creating a tube-like water filled channel. With a negative curvature, the edge of this hole allows for transmission to the inner aspect of the periplasmic space and peptidoglycan. TTPC can take advantage of this action. The TTPC portion can then react easily and at a lower concentration of ppm than the quat amines as well as carrying the other cidal components along such as the glutaraldehyde, OPA, IPA, $ClO_2$. Consequently, TTPC as a quat replacement works via a different mechanism of action, and improves synergy with Glut OPA, $ClO_2$, IPA. This leads to reduced microbial resistance and rebound, decreased environmental toxicity due to using much lower concentrations of all the chemical components, thereby also reducing costs. From a practical viewpoint, the use of synergistic combinations of TTPC and the aforementioned biocides to inhibit bacterial growth is suitable for reduction in biocide' use while being as effective as higher concentrated biocides. As such the addition of TTPC, in lieu of quaternary ammonium, aids in the active sustainability of the biocide process. Therefore reactions are carried out in various types of media, can have enhanced reaction rates, higher yields and unconventional selective reactions.

One last interesting yet obscure issue is that of inadvertent nutrient introduction by glutaraldehyde, in particular, and less so OPA, that will add greater than 50 mg/l of organic carbon to the media over time. Biocides will naturally degrade over time ultimately falling below their MIC, then added carbon will fuel regrowth of the microbes. Quats do not affect this phenomenon, but TTPC does. Unexpectedly, TTPC aids rapid kill and accelerates removal of the necrotic remnants, reducing the remaining bacteria to very low levels prior to biocide degradation, the chance of regrowth is greatly diminished.

A dual biocide approach is extremely important because they minimize the risk of resistant organisms developing, as well as being more effective against recalcitrant organisms. The unique combinations offer a better opportunity for biofilm slime penetration and dispersion, thereby effecting superior cellular penetration enabling an effective cidal dosing at lower minimum kill concentration levels. It allows for multiple. options of kill pathways rather than a single option as is available to single biocides or even dual biocides of related natures. That is the importance of the formulated synergistic effect of cidal biochemical relationships between different chemistries and unusual components.

The above-described addition of a proppant, friction reducing chemical additive, wetting agent, drag reducing agent, and flocculating agent to the core formulation is well-suited for hydraulic fracture or "fracking" to initiate oil and gas production in the shale recovery area, combining biocidal molecules in a synergistic biological chemical system that actively transports itself into the cells, through biofilm and cell wall/membranes, thereby overcoming penetration restraints to improve kill and kill time, without the need for activation or any time or temperature control. This is an effective example of synergistic complementarity.

Although the preferred embodiment uses TTPC in combination with glutaraldehyde, ortho-phthalaldehyde, isopropanol, and chlorine dioxide has been proven effective, one skilled in the art should readily understand that another suitable phosphonium salt might be used in place of TTPC to achieve comparable results. For example, an equal amount of tetrakis (hydroxymethyl) phosphonium sulfate (THPS) may be substituted for TTPC. Having now fully set forth the preferred embodiment, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A biocidal formulation for aqueous addition to fracturing water during secondary oil and gas recovery from a well, comprising orthophthalaldehyde within a range of from 0.25-7% by weight, plus tributyl tetradecyl phosphonium chloride (TTPC) within a range of from 0.24-6% by weight, approximately equal amounts of said orthophthalaldehyde and TTPC, and excipient constituents including triethanol amine, glycol ether, sulfonic acid and water, all mixed in an isopropyl alcohol solution having a pH within a range of from 3 to 9, wherein said biocidal formulation is diluted to within a range of from 50 ppm to 1000 ppm prior to aqueous addition to said fracturing water.

2. The biocidal formulation of claim 1, further comprising a cellulosic proppant selected from the group consisting of methylcellulose, ethylcellulose and hydroxyethylcellulose, and said excipient constituents further comprise a pluronic block copolymer and flocculating agent.

3. The biocidal formulation of claim 1, wherein said isopropyl alcohol is within a range of from 15% to 41%.

4. A biocidal formulation for aqueous addition to fracturing water during secondary oil and gas recovery from a well, consisting of orthophthalaldehyde within a range of from 0.25-7% by weight, tributyl tetradecyl phosphonium chloride (TTPC) within a range of from 0.24-6% by weight, approximately equal amounts of said orthophthalaldehyde and TTPC, a cellulosic proppant selected from the group consisting of methylcellulose, ethylcellulose and hydroxyethylcellulose within a range of from 0.2-0.5% by weight, monomer block copolymer, a triblock non-ionic copolymer, iso-propyl alcohol, and water wherein said biocidal formulation is diluted to within a range of from 50 ppm to 1000 ppm prior to aqueous addition to said fracturing water.

5. The biocidal formulation according to claim 4 wherein said isopropyl alcohol comprises a range of from 10.00%-60.00% by weight.

6. The biocidal formulation according to claim 4 wherein said monomer block copolymer is a non-ionic excipient copolymer surfactant, polyethylene oxide, within a range of concentration of approximately 10 ppm to 100 ppm.

7. The biocidal formulation according to claim 4 comprising a pH within a range of from pH 3 to pH 9.

* * * * *